United States Patent [19]

Moriya et al.

[11] Patent Number: 5,077,475
[45] Date of Patent: Dec. 31, 1991

[54] METHOD FOR QUANTITATIVE EVALUATION METHOD OF OPTICAL ABSORPTION IMAGE FOR DETERMINATION OF RESISTIVITY DISPERSION

[75] Inventors: Kazuo Moriya; Katsuyuki Hirai; Mikio Kimura, all of Tokyo, Japan

[73] Assignee: Mitsui Mining & Smelting Co., Ltd., Tokyo, Japan

[21] Appl. No.: 317,643

[22] Filed: Mar. 1, 1989

[30] Foreign Application Priority Data

Mar. 4, 1988 [JP] Japan ................... 63-49848

[51] Int. Cl.⁵ .......................... G01N 21/00
[52] U.S. Cl. ................... 250/330; 250/341; 356/30; 356/432
[58] Field of Search ............. 250/341, 330; 356/432 T, 30; 324/501

[56] References Cited

U.S. PATENT DOCUMENTS 3,767,304 10/1973 Keenan et al. ............... 356/51
4,581,576 4/1986 Wang ....................... 324/65
4,750,822 6/1988 Rosencwaig et al. ........... 356/445

OTHER PUBLICATIONS

Katsumata et al., "Observation of Micro Defects in GaAs Crystal by VE-IRT Method" Research Report of No 27 Research Meeting, No. 145 Committee of the Japan Society For The Promotion of Science, 2/1985 pp. 54–59.

Karsumata et al., "Measurement Method For Detecting The Distribution of Micro Defects in a GaAs Wafer," Semiconductor World, Jun. 1985 pp. 75–85.

F. W. Voltmer and H. J. Ruiz, National Bureau of Standards Special Publication 400-10, Spreading Resistance Symposium, Proceedings of a Symposium Held at NBS, Gathersburg, MD., Jun. 13–14 1976 pp. 191–199.

Primary Examiner—Constantine Hannaher
Assistant Examiner—Edward J. Glick
Attorney, Agent, or Firm—Bucknam and Archer

[57] ABSTRACT

Disclosed is a quantitative evaluation method of optical absorption image which applies rays of light to a sample to obtain a quantitative optical absorption image without using destructive inspection and which can measure automatically and easily the dispersion of resistivity of the sample by calculating the mean value and standard deviation of the quantitative optical absorption image.

2 Claims, 3 Drawing Sheets

Dispersion of transmission factors of pixels of optical absorption image δ T/T(%). Correlation between dispersion of transmission factors of pixels of optical absorption image and resistivity dispersion in the same region of the absorption image.

LINE PROFILE OF TRANSMISSION FACTOR OF GaAs CRYSTAL

METHOD FOR QUANTITATIVE EVALUATION METHOD OF OPTICAL ABSORPTION IMAGE FOR DETERMINATION OF RESISTIVITY DISPERSION

BACKGROUND OF THE INVENTION

1. Field of the Invention

This invention relates generally to a method of quantitatively evaluating the resistivity dispersion of a crystal sample such as a GaAs crystal by measuring the optical absorption image, and more particularly to a method comprising the steps of obtaining the infrared absorption image which is composed of pixels of a sample of such crystal, the infrared rays used having a 1 um wavelength band using an image processor coupled to a computer, obtaining the absorption coefficient (or transmissivity) corresponding to each of the pixels of this absorption image, simultaneously with calculating the mean value and standard deviation value of the absorption coefficients and obtaining quantitatively values related to the resistivity dispersion of the sample on the basis of these values.

2. Description of the Prior Art

To evaluate performance or characteristics of a GaAs crystal as an electronic device, a method of measuring the resistivity by a 3-terminal guard method and a method for measuring the threshold voltage of each of the FET devices made from a GaAs crystal.

It is known, on the other hand, that the resistivity of an undoped GaAs crystal is related with a deep energy level referred to as "EL2". [(1) "Observation of Fine Defects of GaAs Crystal by VE-IRT Process", T. Katsumata et al., Research Report of No. 27th Research Meeting, No. 145 Committee of the Japan Society for the Promotion of Science; (2) "Measurement Method of Distribution of Fine Defects in a Plane of GaAs Wafer", T. Katsumata et al., "Semiconductor World", June, 1985, p. 75. As to the EL2 level, refer to (1) "Deep Energy Level of III-V Compound Semiconductor", T. Ikoma, Semiconductor Research XXIII, (2) "Non-Uniformity Phenomenon around Dislocation in LEC GaAs", S. Miyazawa, papers of the Japan Crystal Growth Society, Vol. 13, No. 2 & No. 3, (1986), p. 144.] It is also known that there is a relationship between the level EL2 and the absorption of infrared rays of a wavelength 1 um band by GaAs crystal. Evaluation of the crystal by the measurement of the optical absorption coefficient is carried out on the basis of these properties.

However, the method of measuring resistivity by the 3-terminal guard method involves the problems that the same processes are required as those through which a device is actually fabricated and at the same time, an extremely long period of time is necessary for the measurement of characteristics. For example, a measurement time of as long as one week is necessary to measure a wafer having a diameter of 2 inches. Furthermore, this method is a destructive method for inspection.

On the other hand, the method using infrared absorption has been employed conventionally for evaluating the GaAs crystal but this method provides only the transmission image by use of a TV camera but does not provide an absolute transmission factor image, this image being obtained by calculating an absolute transmission factor at each pixel.

SUMMARY OF THE INVENTION

In view of the problems of the prior art technique described above, an object of the present invention is to provide a non-destructive method for the quantitative evaluation of optical absorption image which applied rays of light to a sample such as a GaAs crystal to obtain a quantitative optical absorption image without using a destructive inspection, and calculating the mean value and standard deviation value of transmission factors of the pixels (pixel by pixel) of the quantitative optical absorption image, thus making it possible to estimate automatically the resistivity dispersion of the sample.

To accomplish the object described above, the quantitative evaluation method of optical absorption image according with the present invention comprises uniformly applying infrared rays or the like having a predetermined wavelength in the range of a 1 um wavelength band to a sample such as the GaAs crystal, receiving the rays of light transmitting through the crystal to obtain an absorption image, calculating the transmissivity or transmission factor corresponding to each of the pixels of the absorption image on the basis of the results of receipt of the transmitting light rays and determining the dispersion of resistivity of the crystal on the basis of the mean value and standard deviation of the transmission factor.

In addition the absorption factor a and the transmission factor b have the following relation with the reflection factor being c:

$$a+b+c=1$$

Therefore, if the reflection factor c is constant, the same result will be obtained by determining the absorption factor in place of the transmission factor from the result of light rays received as described above, and this method is obviously embraced within the scope of the present invention.

The above and other objects and novel features of the present invention will become more apparent from the following detailed description when taken in conjunction with the accompanying drawings.

Figure 1:
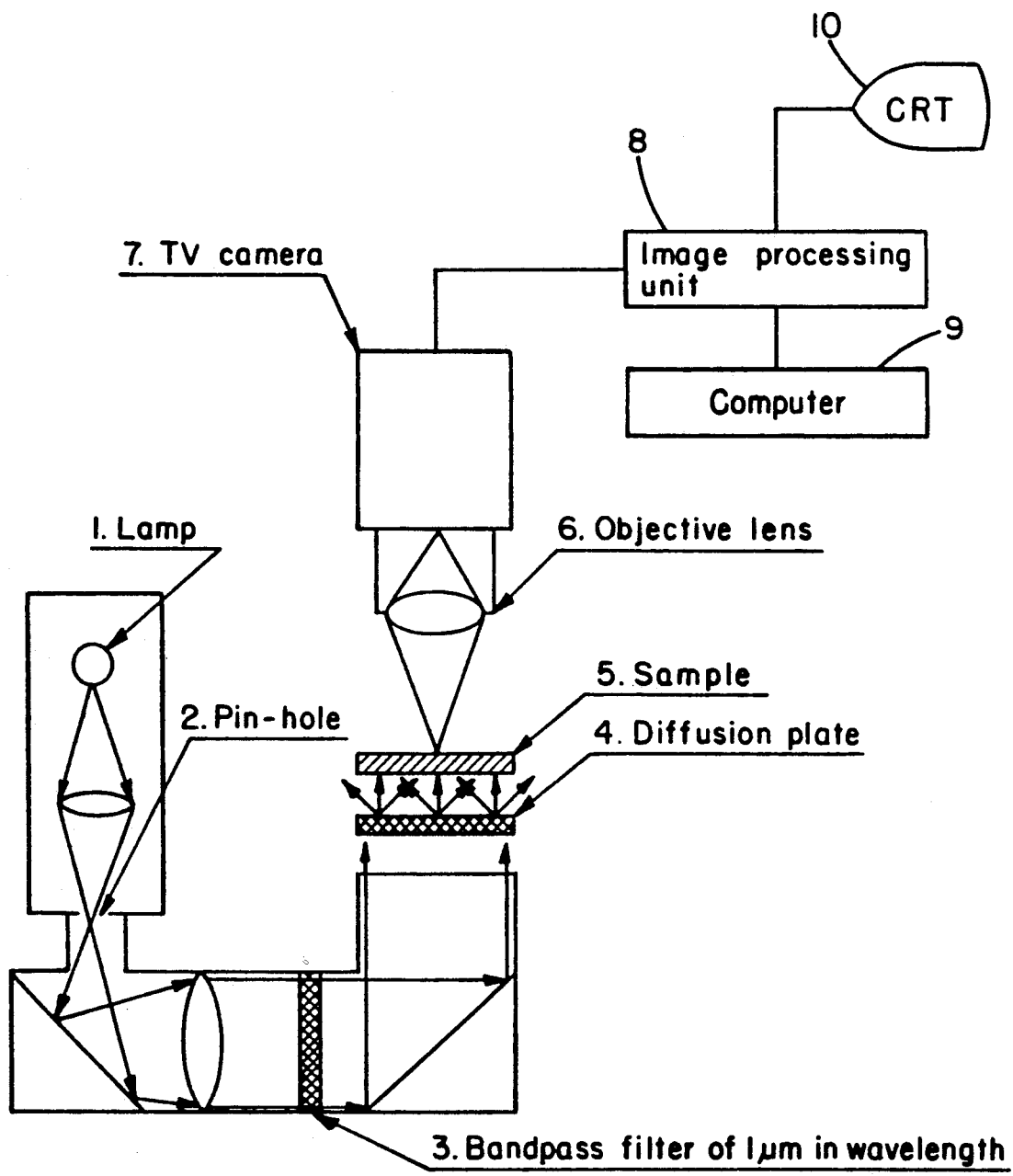
FIG. 1 is a schematic structural view of an apparatus for the quantitative determination of the resistivity dispersion from the absorption image method of the present invention.

Numeral 3 in FIG. 1 designates a bandpass filter of 1 μm in wave length.

Figure 2:
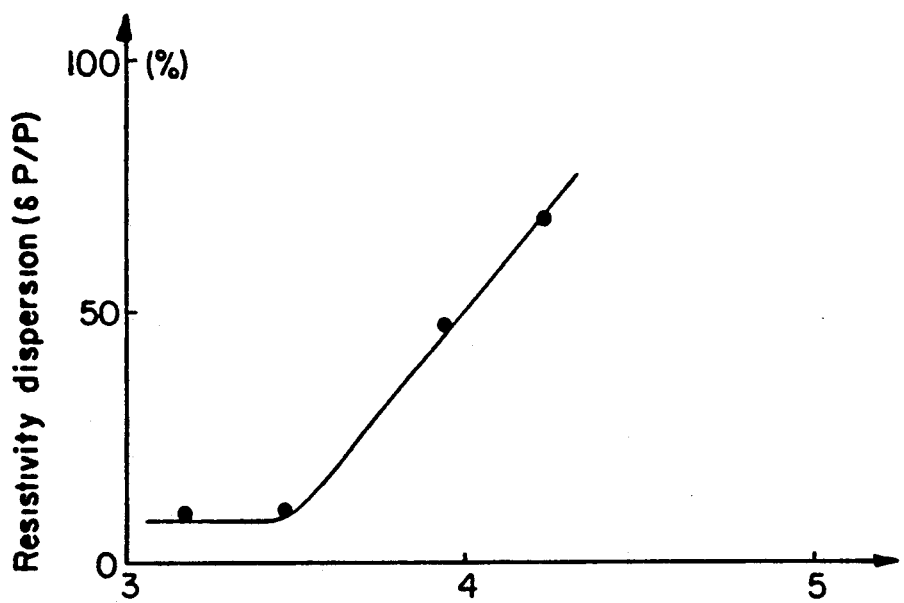
FIG. 2 is a diagram showing the correlation between the dispersion transmission factors of pixels of an optical absorption image and the dispersion of resistivity.

In FIG. 2, there is plotted on the abscissa the dispersion of transmission factors of pixels of optical absorption δT/T% image. On the axis of the ordinate there is plotted the resistivity dispersion δP/P. This figure shows the correlation between the dispersion of transmission factors of pixels of optical absorption image and resistivity dispersion in the same region of the absorption image.

Figure 3:
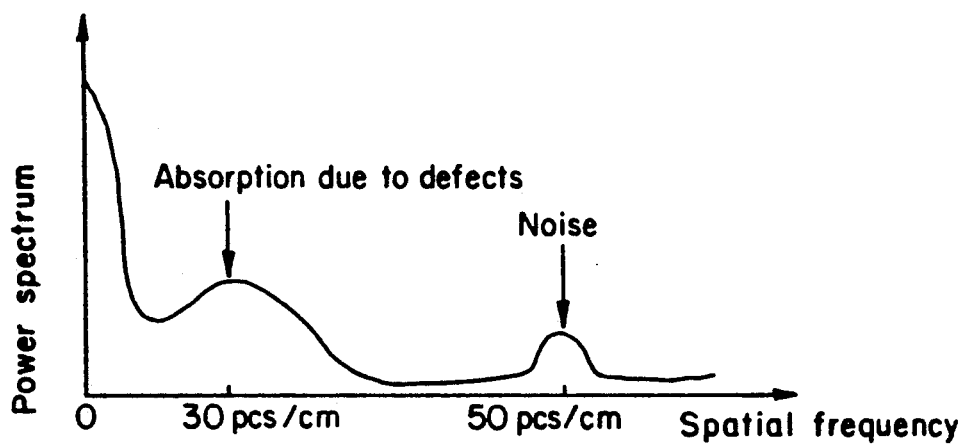
FIG. 3 is a diagram showing a power spectrum of the absorption image by Fourier transform.

FIG. 3 is a diagram showing the power spectrum of the absorption image by Fourier transformation.

DESCRIPTION OF THE PREFERRED EMBODIMENT

First of all, an apparatus for practising the quantitative evaluation method of optical absorption image in accordance with the present invention will be described. FIG. 1 is a schematic view showing the structure of an apparatus for practising the quantitative evaluation method of optical absorption image of the present invention. The method of the present invention is carried out using such an apparatus. A stabilized lamp 1 is used as a light source. After the rays of light from the lamp 1 are focused by a lens, they are passed through a pin-hole 2, again passed through a lens to form parallel rays of light. They are then passed through a bandpass filter 3 of a 1 um wavelength band. The rays of light of this 1 um wavelength band are caused to be incident uniformly on the whole sample 5 through a diffusion plate 4. The rays of light that pass through the inside of the sample 5 are received by a TV camera 7 which is a two-dimensional light rays receiving element through a close-up lens 6. Part of the incident parallel rays of light are absorbed by a defect inside the sample so that the absorption image (transmission image) of the crystal is inputted to an image processing unit 8 through the photoelectric conversion element 7. This data is stored in a recording medium of a computer 9 and after a predetermined processing, is sent to a CRT 10 through the image processing unit 8, where it is displayed as an absorption image that is an image representing the absorption state in the the crystal.

Additionally, in order to quantitatively determine the transmission factor of the crystal from the image data of such an absorption image, the lamp 1 is turned off or the rays of light are prevented from reaching the sample 5 to obtain a dark current image. Furthermore, a sample which has substantially the same thickness as the sample 5 to be measured and whose absorption coefficient (absorption factor/thickness) is substantially zero is placed so as to obtain a transmission image, and computer processing is made on these image data, as well. To make quantitative evaluation of the absorption image, any influence due to dust and scratches on the crystal surface is removed by image processing. The mean value, standard deviation value and the standardized fluctuation ratio (standard deviation/mean value) of the transmission factors of the sample 5 are determined on the basis of the image described above. The value of this fluctuation ratio has a correlation with the dispersion of the resistivity and a quantitative evaluation of the characteristics of the sample 5 can thus be made.

Hereinafter, the present invention will be described in further detail with reference to the following examples.

In the apparatus shown in FIG. 1, a stabilized halogen lamp 1 is used as a light source and the rays of light from this light source are formed into collimated light rays and passed through a bandpass filter 3 of a 1 um wavelength band. The light rays filtered off are caused to be uniformly incident on the entire GaAs crystal 5 through a diffusion plate 4 and the transmission rays of light are received by a TV camera 7 which is a two-dimensional photoelectric conversion element. Thus the rays of light after part of them have been absorbed by the internal defects of the GaAs crystal 5 are received. This image so obtained is inputted to an image processing unit 8 and stored in a recording medium of a computer 9. Thus an image data I is obtained.

Next, to measure the non-uniformity of the incident light source and lens and to measure the reflection on the surface of the GaAs crystal 5, a wafer which has the same thickness as the measured sample 5 and whose absorption coefficient is almost zero is placed in the position where the sample 5 was placed and a transmission image is obtained by treatment in the same manner as sample 5. Thus an image data II is obtained. Finally, the rays of light from the halogen lamp 1 are cut off to obtain a dark current image of the two-dimensional photoelectric conversion element 7 to obtain an image data III.

The following equation is used for each pixel of the image data on the basis of the data described above to obtain an image data representing the absolute transmission factor, and this image data is transferred to a CRT 10 for display:

$$\text{transmission factor} = \frac{(\text{image data I}) - (\text{image data III})}{(\text{image data II}) - (\text{image data III})} \times 100(\%)$$

The transmission factors are not uniform in the crystal having internal defects. Then, T the mean value of the transmission factors and standard deviation $\delta T$ the standard deviation value of the transmission factor are obtained and then the standard deviation/means value ($\delta T/T$) is obtained. There is the relation shown in FIG. 2 between this value $\delta T/T$ and the ratio of the $\delta$ the mean value of resistivities to its standard deviation $\delta \rho$, that is, $\delta \rho/\rho$ (this value $\delta \rho/\rho$ will be referred to as "resistivity dispersion" in this invention. Naturally, the two measurements are made in the same measuring region of the crystal. Therefore, the measuring area is on the order of several millimeters square. The problem with this method is the influence of dust and scratch that might exist on the sample surface. Therefore, this influence is eliminated by the following two methods.

The first method subjects the absorption image to Fourier transform. The absorption image itself due to the absorption influence of the GaAs crystal changes gradually. Therefore, when the output image data of the two-dimensional photoelectric conversion element is subjected to FFT (Fast Fourier transform), the influence of the dust and scratch appears at the portions where the spatial frequency is high, as shown in the diagram of FIG. 3. Therefore, the noise component can be eliminated by removing any high frequency components in the Fourier transform image and then making inverse Fourier transform.

Figure 4:
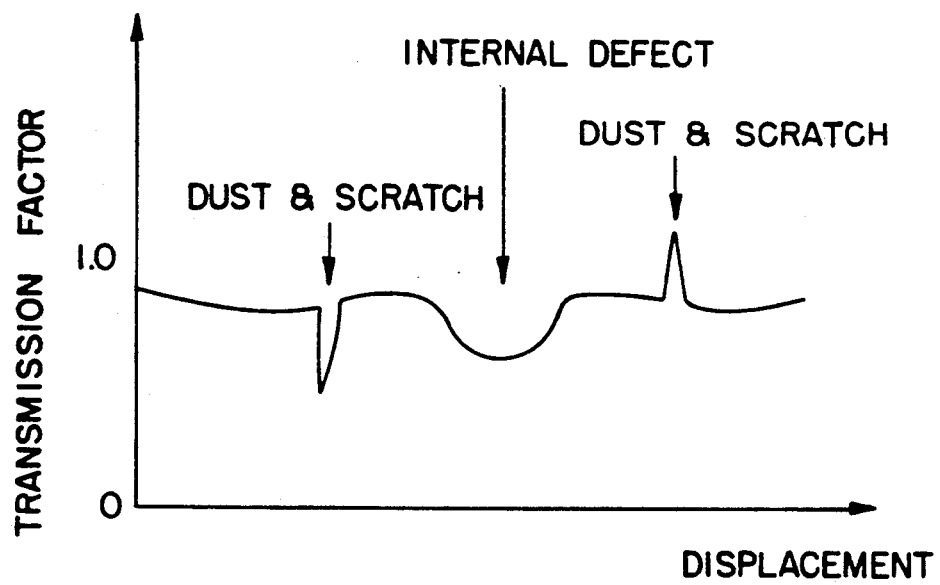
FIG. 4 is a diagram showing the line profile of the transmission factor of a GaAs crystal.

The second method is to determine whether or not the transmission factors fall within a predetermined range. FIG. 4 is a diagram showing a line profile of the transmission factors of the GaAs crystal. As can be seen from this diagram, the change of the transmission factors due to the internal defects falls within a predetermined range. However, the dust and scratch are observed as an abnormally great absorption or conversely (as luminescence in case the transmission factor being at least 1). Therefore, the values deviating greatly from the mean absorption range are eliminated and $\delta T/T$ is calculated so that the noise component can be eliminated.

Example 2: The same result as in Example 1 can be obtained by following the procedure of Example 1 except that a CCD camera or the like is used in place of the TV camera used in the embodiment described above. It is also possible to obtain the image data by scanning the sample by use of a unidimensional photodetector such as a line sensor or a zero-dimensional photodetector such as a photomultiplier (PM tube).

Though the examples described above deal with the measurement of the GaAs crystal, the method of the present invention can be employed by when the wavelength and the sample are changed. Accordingly, the method of the present invention can be changed to a general quantitative evaluation method.

As described above, the present invention can measure the dispersion of the resistivity within a few minutes by deriving the mean value of the transmission factors of the sample and the standard deviation value of the transmission factors. Moreover, the method of the present invention is a non-destructive measuring method and can drastically reduce the cost (to about 1/1000) of measurement.

Although the present invention has been described in its preferred form, it will be obvious to those skilled in the art that various changes and modifications may be made without departing from the spirit or scope of the following claims.

What is claimed is:

1. A method for the quantitative evaluation of optical absorption image for determining resistivity dispersion consisting of the steps of:
   uniformly applying light of predetermined wavelength having a constant intensity to the entire exposed surface of a crystal sample;
   receiving the light rays transmitting through said crystal sample to obtain an optical absorption image of said crystal sample:
   calculating the transmission factors of the pixels of the optical absorption image on the basis of the result of receipt of the transmitting light rays; and
   determining the resistivity dispersion of said crystal sample on the basis of the mean value of said transmission factors and the standard deviation value thereof.

2. A method according to claim 1 wherein said crystal sample is a GaAs crystal and said light rays are infrared rays having a 1 um wavelength band.

* * * * *